United States Patent [19]

Platt et al.

[11] Patent Number: 4,493,825

[45] Date of Patent: Jan. 15, 1985

[54] PURIFIED AND ANTIGENICALLY SELECTIVE VACCINES FOR DOMESTIC ANIMALS

[75] Inventors: Kenneth B. Platt; David E. Reed, both of Ames, Iowa

[73] Assignee: Iowa State University Research Foundation, Ames, Iowa

[21] Appl. No.: 432,967

[22] Filed: Oct. 5, 1982

[51] Int. Cl.³ .................... A61K 39/00; A61K 39/12; A61K 39/02

[52] U.S. Cl. ....................................... 424/88; 424/89; 424/92

[58] Field of Search ...................... 424/85, 88, 89, 92, 424/93; 436/533–535, 827, 828

[56] References Cited

U.S. PATENT DOCUMENTS 4,189,466 2/1980 Ainis et al. ............................ 424/12
4,230,685 10/1980 Senyei et al. ......................... 424/12

*Primary Examiner*—Sidney Marantz
*Assistant Examiner*—Shawn P. Foley

[57] ABSTRACT

Purified antigenically selective vaccines for domestic animals are prepared from microorganism cultures containing the immunizing agent by first complexing the immunizing agent with micro-particles having bound IgG antibodies specific for the immunizing agent, separating the resulting complex, and preparing a vaccine directly therefrom containing the antigen-antibody complex. The micro-particles preferably have Protein A in their outer surfaces for binding to the specific antibodies. The complex-containing vaccines provide effective immunization. The method and the resulting vaccines are particularly useful in preparing viral and bacterial subunit vaccines.

8 Claims, No Drawings

PURIFIED AND ANTIGENICALLY SELECTIVE VACCINES FOR DOMESTIC ANIMALS

GRANT REFERENCE

The invention described herein was made in the course of work under grant from the United States Department of Agriculture, No. 58-519B-1-0999.

FIELD AND OBJECTIVES OF INVENTION

The field of this invention is animal vaccines prepared from aqueous microorganism cultures. The desired immunizing agent which has been propagated by a culture procedure may be a virus, a bacteria, or other microorganism such as a protozoa. The method is highly advantageous for preparing vaccines from soluble protein or glycoprotein antigens derived from virus or bacteria.

The objectives of this invention involve the recovery of the selected immunizing agent in purified form, and its incorporation in a parenteral vaccine of effective immunogenicity. More specifically, it is an objective to provide a method in which the specific immunizing agent can be recovered and incorporated in substantially pure form in a vaccine while at the same time reducing the required number of preparatory steps, and thereby reducing the cost of the preparation of the vaccine. These objectives are particularly important with respect to subunit viral and bacterial vaccines of practical and commercial use of which has been limited by the high cost of preparation. In the preparation of vaccine from bacterial cells, the cells can be readily separated from the culture media suspensions by centrifigation, and after separation, they can be washed to remove soluble residues. Solubilized bacterial antigens, viruses, and subunit viral proteins are much more difficult to prepare as purified concentrates.

Viruses for vaccine use are produced in cell-containing media, adapted tissue cells or other cells serving as the host for the propagation of the virus. The cells can be lysed to liberate the virus, but it is difficult to efficiently separate the viral particles for the other solids of the media residues. Such separation is even more difficult where the viral protein has been solubilized, such as by the action of a nonionic detergent, the antigenic proteins being in solution together with other soluble substances. Similar problems are encountered when antigenic components of bacteria are solublized, or where the desired antigen is produced in soluble form by a genetic engineering procedure, such as the culturing of cells containing plasmids providing genetic units producing the desired antigenic protein.

There has been a recognized need for better methods of recovering and concentrating the immunizing agents used in animal vaccines. This need has been particularly evident with respect to non-cellular immunizing agents such as virus, and solubilized antigenic protein derived from virus or bacteria.

SUMMARY OF INVENTION

It is known that IgG antibodies that bind selectively to specific antigenic protein can be prepared and used for the separation of the antigenic protein. For this purpose, Protein A has been used as a surface-component of the micro-particles to be employed for the separation. For example, Protein A may be coupled to beads of a chromatographic adsorbent such as cross-linked agarose gel beads. The Protein A binds with the Fc regions of the specific antibodies, leaving the Fab arms free for binding with the antigenic protein. Heretofore, however, after separation of the virus by adsorption on the antibody coated particles, the antigenic protein is recovered by breaking the complex, such as by the use of a suitable eluting agent in column adsorption procedures. It is not heretofore been recognized that the antigen-antibody-Protein A-carrier particle complex can be directly used as a vaccine. The method and vaccines of this invention are based in part on the discovery that after adsorption of the antigen further processing is not necessary, and that vaccines providing effective immunization can be directly prepared from the adsorption complex. This is surprising since the immunizing activity of the antigenic protein would have been thought to have been interfered with by the antibody binding.

The method of this invention and the vaccines produced thereby can be applied with particular advantage to the preparation of subunit viral vaccines. This invention provides an efficient way of preparing such vaccines on a commercial basis. This is important because subunit viral vaccines can be used in conjunction with programs for eradication of bacterial and viral diseases. The immunity produced by a subunit vaccine can be distinguished from the immunity of natural infection because a larger complement of antibodies will be present after natural infection.

DETAILED DESCRIPTION

The antibody-binding micro-particles used in preparing vaccines according to the present invention may comprise killed bacterial cells having a protein substance in their cell walls capable of selective binding to the Fc regions of the antibodies. For example, it may be the substance known as Protein A, and the cells providing Protein A in the cells walls may be Staphylococcus aureus. Preserved (e.g. formalinized) cells of *S. aureus* (Cowan 1 Strain) are available from Calbiochem-Behring Corp., San Diego, Calif.; or from Bethesda Research Laboratories, Inc., Gaithersburg, Md. Alternatively, other killed bacterial cells can be used which have a cell wall protein binding to the Fc regions of the antibodies.

The protein A or other Fc-binding bacterial protein may be immobilized on synthetically prepared microparticles or microspheres, such as the chromatographic gel beads used in chromatography adsorption columns. Protein A or similar protein may be chemically coupled to the substance forming the microspheres. A commercial product of this kind is available from Pharmacia Fine Chemicals, a division of Pharmacia, Inc., Piscataway, N.J., being sold as Protein A-Sepharose CL-4B, which comprises Protein-A covalently coupled to the cross-linked agarose gel beads. Alternatively, microspheres providing Protein A in their outer surfaces can be prepared by mixing the Protein A with aqueous albumin and forming the mixture into microspheres by the hot oil method described in U.S. Pat. No. 4,230,685, or as described in Scheffel, et al, *J. Nuclear Med.*, Vol. 13, No. 7, 498–503 (1972). For the purpose of the present invention if the procedure of U.S. Pat. No. 4,230,685 is followed, the magnetic particles will be omitted from the microspheres, the resulting procedure being similar to that described by the cited Scheffel, et al reference.

The antibody preparations useful in the present invention are those which contain one or more specific antibodies having Fb regions reacting with Protein A or similar protein on the surfaces of the micro-particles. For example, Protein A is able to interact with a wide variety of IgG molecules from various species. The antibodies may be prepared in the same species of animals from which the vaccine is to be used, such as cattle, sheep, or swine. A hyperimmune serum can be prepared according to known procedures. See, for example *Methods in Immunology and Immunochemistry*, I, 209–224 (1967, Academic Press). Where the specific antibody of the species to be immunized are not reactive with the Protein A, the antibodies can be prepared in another host animal. For example, rabbits can be used, since the rabbit immunoglobulins binding to Protein A include all subclasses of IgG. Also, mouse monoclonal antibodies specific for the desired antigen can be employed.

The antibodies can be readily removed from dilute solutions thereof, such as animal sera, by contacting the solutions with the micro-particles. This contacting reaction can be carried out in a column or on a batch basis. The resulting separated complex of the antibody-Protein A-carrier particle is then used to prepare the vaccine, and is hereinafter referred to as the separator complex.

The immunizing agent is prepared by in vitro microorganism culture. Virus may be propagated in cell culture in an aqueous medium, and the virus liberated by rupturing (lysing) cells, such as by sonication. Viral particles are liberated into the aqueous medium, and the residue solids of the cell mass can be separated by centrifigation, leaving the viral particles in the aqueous medium, which will also contain other components such as unwanted antigenic protein and other culture residue substances. For the preparation of a subunit viral vaccine, the virus may be dissolved by addition of a solubilizing agent, such as nonionic detergent, or a proteolytic enzyme. Antigens may also be extracted from the membranes of virus infected cells with nonionic detergents.

The antibodies immobilized on the micro-particles will be specific to the desired immunizing agent, such as antibodies which bind to the whole virus, or antibodies which bind to selected antigenic protein constituents of the solubilized virus or extracted antigens. The antigens may be envelope glycoproteins or one or more specific glycoproteins or other protein constituents of the virus.

The method of this invention can also be applied to the preparation of vaccines from specific antigens produced by genetic engineering procedures. The plasmid-containing cells are propagated in aqueous medium to produce the antigen, which may have been at least partly liberated into the aqueous media. Usually, the cells will be lysed to further liberate the soluble antigen, and the cell mass removed to provide an aqueous solution of the antigen which will also contain unwanted antigenic protein and other culture residue substances. This solution is then processed in the same manner as described above for subunit viral protein.

In still another application, the method of this invention may be used for the recovery of protozoan parasites such as Babesia species which occur in red blood cells. These agents can be produced in large quantities by infecting splenectomized animals or by in vitro propagation. Red blood cells containing the agents are first lysed releasing the protozoan. The liberated protozoans and those protozoans that occur extracellularly are then aggregated by specific antibodies adsorbed to protein A immobilized on microparticles or to protein A contained on the surface of *Staphylococcus aureus*. The aggregated antigen-antibody complexes are separated from the particulate and soluble remnants of red blood cells by differential centrifugation and washing.

The reaction of the immunizing agent in the aqueous admixture with the separator complex may be carried out on a batch basis or in a column. In a batch reaction, the antigenic protein in solution will bind to the separator complex so that the resulting antigenic complex can be readily separated from the residual solution by standard separating procedures such as centrifigation. Where the reaction is carried out in a column, the antigen will be held up by selective adsorption on the separator complex, while a residual solution will pass through and out of the column. The column material containing the adsorbed antigen can then be removed from the column, after washing, if desired, and used to prepare the vaccine in the same manner as the separated precipitate from the batch reaction. Preferably, a sufficient amount of the separator complex is present to react with all of the antigenic protein. If desired, excess separator complex can be present, and such excess separator complex may be separated with the antigenic protein complex, and may remain in the preparation for vaccine use. Preferably, however, any such excess is kept to a minimum to reduce costs in preparing the vaccine.

After recovery, the complexed immunizing agent is prepared in vaccine dose form for administration to the domestic animal. For example, the particulate antigenic complex may be suspended in an injectable liquid carrier, such as a sterile phosphate-buffered saline solution, as used for parenteral injections. Additionally, however, standard adjuvant compositions can be combined with the complexed immunizing agent to enhance the immunogenic response. For example, an aluminum hydroxide adjuvant can be employed, or an oil-type adjuvant such as vegetable oil adjuvant, Freund's Incomplete Adjuvant, etc.

The method of this invention and the vaccines which can be produced thereby are further illustrated by the following examples.

EXAMPLE I

A subunit vaccine for immunizing pigs against Pseudorabies was prepared as follows:

Preparation of $R_2$ and $R_3$ Antigens

1. Pseudorabies virus was progated by cultivation of the virus in a pig kidney cell line. The virus infected cells are harvested when 100% of the cell monolayer shows cytopathic effect.

2. The cells are washed and then extracted with a 1% solution of Triton-X-100 prepared in Tris/Tricine buffer 0.025 M pH 8.6. The detergent solution is added at the rate of 1 ml per 1 ml cell volume. Cell volume is determined by pelletting the cell suspension at 800 xg for 20 minutes. The cells are then resuspended and sonically disrupted. The disrupted suspension is then gently agitated for a minimum of 1 hour at 4° C. The suspension is then clarified by low speed centrifugation followed by centrifugation at 100,000 xg for 90 minutes. The clear middle layer is harvested and used as crude antigen. The upper cloudy layer is first treated with freon to remove lipids and also used as crude antigen. The protein concentration of this preparation usually ranges between 6 and 7 mg/ml. The two layers were combined.

3. Glycosylated viral antigens which include antigens $R_2$ and $R_3$ are extracted from crude antigen with lentil bean lectin. The lectin is commercially supplied conjugated to agarose beads (E-Y Laboratories, 127 N. Amphledt Blvd., San Mateo, Calif. 94401). Equal volumes of agarose-lectin and the combined crude antigen are mixed together and permitted to react overnight at 4° C. The preparation is then washed to remove non-absorbed antigen. The washed lectin-agarose is then treated with a 2% solution of α-methyl mannopyranoside to elute the glycosylated viral proteins.

The porcine immunoglobulins specific for the PR virus glycosylated proteins $R_2$ and $R_3$ were reacted with commercially supplied formalinized *Staph. aur.* (Cowan strain 1) obtained from Bethesda Research Laboratories, Inc. The immunoglobulin (6 mg/ml) was added to a 10% suspension of the *Staph. aur.* in 0.1 M phosphate-buffered saline pH 7.2 at the rate of 0.1 ml immunoglobulin to 1.0 ml of bacterial suspension. The mixture was gently agitated at 4° C. overnight. The following morning the immunoglobulin-coated bacterial cells were washed free of non-attached immunoglobulin and mixed with a lectin purified preparation of PR virus antigens containing the glycosylated immunogens $R_2$ and $R_3$. The *Staph. aur.* suspension was then washed to remove the unbound PR viral antigens. The resulting preparation was then used with or without adjuvant as a vaccine for pseudorabies in pigs.

Seven weaning pigs were randomly split into a control group of 3 and 2 vaccine groups of 2 pigs each. The first vaccine group received 1 ml of the above vaccine preparation mixed in an equal volume of Freund's incomplete adjuvant, designated "VAC(FIA)". The second vaccine group received 1 ml of vaccine without adjuvant, designated "VAC". Both vaccine groups received a second inoculation 3 weeks after the first and were subsequently challenged 3 weeks later by nasally administering $10^{8.7}$ PFU of virulent PR virus. The effectiveness of the vaccine was demonstrated by monitoring the anamnestic antibody response of the vaccinates, and the virus secretion patterns and weight gain of control and vaccinated pigs. The data obtained is summarized below in Tables A and B. The antibody response was determined by the serum neutralization plaque reduction method.

TABLE A

Antibody Response of Vaccinated and Control Pigs Before and After Challenge with $10^{8.7}$ PFU Virus

| Time (Days + and − day of challenge) | Serum Neutralizing Antibody Titers of Pigs[a] | | |
|---|---|---|---|
| | VAC (FIA)[b] | VAC[c] | Controls[d] |
| −14 | 0 | 0 | 0 |
| 0 | 2.0 | 0 | 0 |
| 4 | 2.6 | 2.6 | 0 |
| 10 | 64.0 | 45.2 | 22.6 |
| 17 | 31.8 | 45.2 | 22.6 |

[a,b,c]n = 2, VAC (FIA) = Pigs receiving vaccine with Freund's Incomplete Adjuvant, VAC = Pigs receiving vaccine without adjuvant.
[d]n = 3 Through day 4 then n = 2
[a]Serum titers determined by the serum virus neutralization/plaque reduction test.

TABLE B

Rate of Weight Gain of Vaccinated and Control Pigs Before and After Challenge with $10^{8.7}$ PFU Virus

| Time Period | Rate of Gain (lbs/day) | | |
|---|---|---|---|
| | VAC (FIA)[a] | VAC[b] | Controls[c] |
| Day 0–4 | −0.13 | −0.500 | −0.83 |
| Day 4–10 | +1.41 | +1.83 | −0.12 |
| Day 4–17 | +1.52 | +1.58 | +0.85 |

[c]n = 3 through day 4 then n = 2
[b]n = 2, VAC = Pigs receiving vaccine without adjuvant.
[a]n = 2, VAC (FIA) = Pigs receiving vaccine with Freund's Incomplete Adjuvant.

EXAMPLE II

A vaccine for immunizing pigs against pseudorabies was prepared, using the general procedure of Example I, except that the vaccine contained a larger number of antigenic proteins. The difference between the vaccine preparations of Examples I and II is that the vaccine of Example II contains the antigens that are selectively bound by lentil bean lectin.

To accomplish this the immunoglobulins that are used to coat the formalinized Protein A—containing *Staph aureus* were derived from serums of pigs that had been immunized with Lectin PRV vaccine.

The lectin PRV vaccine is produced as indicated above in Paragraphs 1 and 2 of "Preparation of $R_2$ and $R_3$ Antigens" and as further indicated below.

The glycosylated viral antigens as obtained in Example I are extracted from crude antigen with lentil bean lectin. The lectin is commercially supplied conjugated to agarose beads. Equal volumes of agarose-lectin and the combined crude antigen are mixed together and permitted to react overnight at 4° C. The preparation is then washed to remove non-adsorbed antigen. This preparation is then mixed 1:1 with Freund's incomplete adjuvant and used as vaccine.

The results are summarized below in Tables C and D.

TABLE C

Antibody Response of Vaccinated and Control Pigs Before and After Challenge with $10^{8.7}$ PFU Virus.

| Time Days + and − day of challenge | Serum Neutralizing Antibody Titers[a] | |
|---|---|---|
| | Vaccinated Pigs[b] | Controls[c] |
| −21 | 5.6 | 0 |
| −3 | 7.9 | 0 |
| 0 | 5.6 | 0 |
| +4 | 4.7 | 0 |
| −10 | 75.0 | |
| +17 | 63.1 | |

[a]Serum titers determined by the serum neutralization/plaque reduction test
[b]n = 4
[c]n = 3, all controls died between day 5 and day 6 post virus challenge

TABLE D

Rate of Weight Gain of Vaccinated and Control Pigs Before and After Challenge with $10^{8.3}$ PFU Virus

| Time Period[a] | Rate of Gain (lbs/day) | |
|---|---|---|
| | Vaccinates[b] | Controls[c] |
| Day −12 thru 0 | +1.79 | +1.83 |
| Day 0 thru 4 | −1.85 | −2.40 |
| Day 0 thru 6[d] | −1.50 | —[e] |
| Day 6 thru 17 | +1.95 | |

[a]Day 0 = day of challenge
[b]n = 4
[c]n = 3
[d]Day 6 = the last day with a recorded weight loss
[e]All controls died between days 5 and 6

EXAMPLE III

A bovine herpesvirus-1 (IBR) vaccine (Lupton and Reed, U.S. Pat. No. 4,291,019) is purified further by use of the Protein A separator complex. Antibody used in this procedure is monospecific for the immunizing protein(s) of the virus and is prepared by conventional protein purification methods or by the monoclonal antibody technology. The higher purity of an IBR vaccine processed through the separator complex will allow easy development of diagnostic serologic tests, which can be used to differentiate naturally infected cattle from vaccinated cattle.

EXAMPLE IV

The immunizing proteins of Brucella are identified, and monospecific antibody against the immunizing protein(s) are prepared and used in the separator complex. This will allow easy production of a purified subunit vaccine for Brucella by passing solubilized Brucella organisms over the separator complex. Such a vaccine would allow development of a Brucella diagnostic test utilizing any of the antigens not included in the vaccine. This diagnostic test would be significantly better than the current diagnostic tests in the Brucella control program. In the current test, vaccine response is differentiated from natural exposure (infection) response by multiple serological testing. This has not been satisfactory because of the time required. A control program built around a separator complex purified vaccine would utilize diagnostic tests which would not necessarily be based on multiple serological tests but would be based upon the presence or absence of antibody against the diagnostic antigens.

EXAMPLE V

The current whooping-cough vaccine for humans contains inactivated whole *B. pertussis* organisms. This vaccine causes some local toxic reaction and occasional cases of allergic encephalitis. An extract vaccine has been proposed to circumvent these undesirable side-effects. See Swick, et al., *New Developments with Human and Veterinary Vaccines*, 143-155 (1980, Alan R. Liss, Inc.). The separator complex of this invention can be used against the immunizing fraction of *B. pertussis*. This will yield rapid purification of the immunogen and, more importantly, separation of the immunogen from the allergenic and toxogenic fractions. Similarly, the separator complex can be used for preparation of vaccines for foot and mouth disease (FMD) of cattle. In FMD there are allergic reactions caused by media components (horse serum) and cell components (baby hamster kidney cell cultures) which are reported to cause anaphylactic reactions in vaccinated cattle. These undesirable components can be eliminated from the vaccines.

EXAMPLE VI

The method of this invention can also be used to extract specific protective antigens from protozoans such as *Babesia bovis*, a cattle pathogen. To accomplish this a separator complex is prepared containing conventional immunoglobulins or monoclonal antibody specific for protective antigens. *Babesia bovis*-infected red blood cells are then produced by infecting splenectomized cattle with the pathogen or by propagating the protozoan in vitro (Erp et al., 1978; *Am. J. Trop. Med. Hyg.* 27, 1062-1064). The infected red blood cells are separated from serum and/or culture components, washed, and solubilized by sonification and/or treatment by non-ionic detergents such as Triton-X-100. The separator complex is then added to the solubilized preparation as described in example I and the specific antigen(s) is (are) removed. The recovered antigen(s) that are bound to the separator complex are then washed to remove unabsorbed materials and used as vaccine.

EXAMPLE VII

Specific protective solubilized viral antigen can also be retrieved by separator complexes that do not consist of Staph A. An example of such a separator complex is Protein A covalently linked to Sepharose CL-4B (Pharmacia Fine Chemicals, Piscataway, N.J.) and to which has been bound an immunoglobulin of particular antigen specificity. The separator complex is then used to selectively remove specific antigens from solubilized crude virus antigen preparations by the batch technique as described in Example I. The separator complex containing antigen is washed to remove unbound PR viral antigens and the resulting preparation is used with or without adjuvant as a vaccine for pseudorabies in pigs.

EXAMPLE VIII

Micro-particles containing immobilized protein A are prepared from serum albumin and pure Protein A. The albumin employed is preferably a serum albumin of the species of animal to which the vaccine is to be administered, such as swine albumin for a swine vaccine, etc. The Protein A may be obtained from Pharmacia Fine Chemicals, Piscataway, N.J. A modification of published procedures may be used, as described in U.S. Pat. No. 4,230,685, and/or Scheffel, et al, *J. Nuclear Med.*, Vol. 13, No. 7, 498-503 (1972). For example, the serum albumin may be dissolved in distilled water to an albumin concentration of about 20-25%, viz., 200 milligrams (mg) per milliliter (ml) of water gives a 20% solution. Into this aqueous albumin solution there is added the water-soluble Protein A in an amount of about 50-60 milligrams (mg) per milliliter (ml) of solution. This aqueous mixture is then dispersed in a vegetable oil, such as cottonseed oil, to form a fine water-in-oil emulsion. For example, 1.0 parts of the aqueous solution may be dispersed in 120 parts of vegetable oil, and the emulsion homogenized by sonication. The homogenate is added dropwise to a constantly stirred bath of vegetable oil, such as cottonseed oil, maintained at a temperature of 120°-125° C. for 10 to 15 minutes. The resulting microspheres are recovered by centrifigation, and washed to remove the vegetable oil on the surface of the particles, using an oil solvent such as diethyl ether.

The resulting washed microspheres provide surfaces containing Protein A, and therefore can be used to prepare vaccines according to the foregoing examples, as the substitute for the *S. aureus* cells or the Protein A Sepharose column beads.

We claim:

1. The method of preparing a purified antigenically selective vaccine for a domestic animal, comprising:
   (a) preparing by in vitro microorganism culture an aqueous admixture of the desired animal disease immunizing agent together with other antigenic protein and culture residue substances, said immunizing agent being selected from the class consisting of pathogenic microorganisms and immunizing antigenic protein derived therefrom;
   (b) complexing the IgG antibodies specific for the said immunizing agent with micro-particles having outer surfaces containing protein A selectively binding to the Fc region of the IgG antibodies so that the antibody Fab regions of the resulting first complex are oriented for binding reaction;

(c) reacting said immunizing agent in said aqueous admixture with said first complex to form a second complex;

(d) recovering said second complex from said aqueous admixture in purified form; and (e) preparing a parenteral vaccine from said second complex by suspending an immunologically effective amount thereof in a parenterally-injectable liquid carrier for animal vaccines, said second complex containing said IgG antibodies in complexed relationship with said immunizing agent.

2. The method of claim 1 in which said immunizing agent is whole virus.

3. The method of claim 1 in which said immunizing agent is antigenic protein in aqueous solution in said admixture.

4. The method of claim 1 in which said immunizing agent is pseudorabies virus.

5. The method of claim 1 in which said immunizing agent is viral antigenic glycoprotein in aqueous solution in said admixture.

6. The method of claim 1 in which said liquid vaccine carrier contains an immunization-promoting adjuvant.

7. The vaccine produced by the method of claim 1.

8. The vaccine of claim 7 which also contain an immunization-promoting adjuvant.

* * * * *